(12) United States Patent
Thompson

(10) Patent No.: US 7,674,419 B2
(45) Date of Patent: Mar. 9, 2010

(54) METHOD AND APPARATUS FOR MAKING FOOT IMPRESSIONS

(76) Inventor: Terry Thompson, 1218 Stewart Rd., Salem, OH (US) 44460

( * ) Notice: Subject to any disclaimer, the term of this patent is extended or adjusted under 35 U.S.C. 154(b) by 521 days.

(21) Appl. No.: 11/800,001

(22) Filed: May 4, 2007

(65) Prior Publication Data

US 2008/0274219 A1 Nov. 6, 2008

(51) Int. Cl.
*B29C 43/02* (2006.01)
(52) U.S. Cl. .............. 264/321; 264/223; 264/DIG. 30; 425/2
(58) Field of Classification Search ............... 264/223, 264/320, 321, DIG. 30; 425/2; 12/142 N, 12/146 M; 33/514.2, 515
See application file for complete search history.

(56) References Cited

U.S. PATENT DOCUMENTS

| 584,693 | A | | 6/1897 | Marshall |
| 1,044,171 | A | | 11/1912 | Guilford |
| 1,638,696 | A | | 8/1927 | Lewis |
| 1,682,579 | A | * | 8/1928 | Oliver ........................ 33/3 C |
| 2,177,304 | A | | 10/1939 | Murray |
| 2,487,965 | A | | 11/1949 | Dresser |
| 2,613,398 | A | | 10/1952 | Crowell |
| 2,891,285 | A | * | 6/1959 | Kaplan ........................ 264/223 |
| 3,358,332 | A | * | 12/1967 | Downey ..................... 425/394 |
| 3,458,898 | A | | 8/1969 | Casparis |
| 4,139,337 | A | | 2/1979 | David et al. |
| 4,747,989 | A | | 5/1988 | Peterson |
| 5,282,328 | A | * | 2/1994 | Peterson ...................... 36/154 |
| 5,593,699 | A | | 1/1997 | Grassi |
| 5,928,673 | A | | 7/1999 | Ryan |
| 6,564,465 | B1 | * | 5/2003 | Ward ........................... 33/515 |
| 7,125,509 | B1 | * | 10/2006 | Smith ........................ 264/223 |

* cited by examiner

*Primary Examiner*—Robert B Davis
(74) *Attorney, Agent, or Firm*—Frederic E. Naragon

(57) ABSTRACT

A method and apparatus for the making of an impression of a person's foot in foam to be used in the manufacture of orthotics comprising in combination a box of foam that will be deformed by the person's foot during the making of a foot impression, placed in foam box receptacle that is supported on a base and which can adjustably swivel or rotate so that the person's knee, ankle and foot will be put in a neutral position and when in use the person is placed in a seated position and a box of foam is placed in the receptacle and a strap assembly is used to exert a downward force on the person's lower leg, the strap being secured to a lever arm used to exert a downward pressure and engage with a block arm which correspondingly exerts a downward force on a block situated above the box of foam and which pushes the foot down into the foam and wherein the block is slideable transversely to the box of foam to align with the arch of the person's foot and to insure that the block exerts its downward pressure evenly and directly on the person's foot.

10 Claims, 5 Drawing Sheets

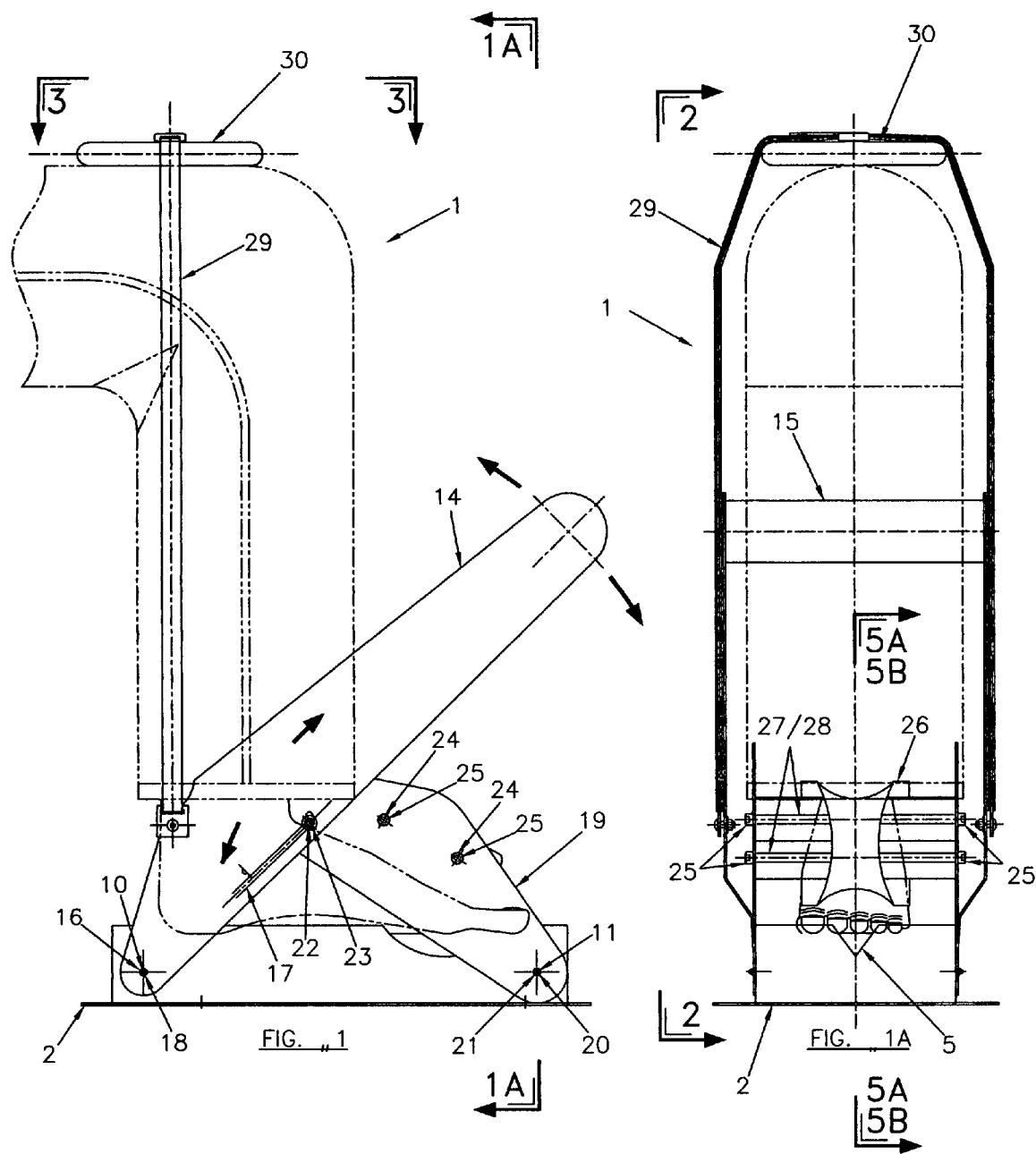

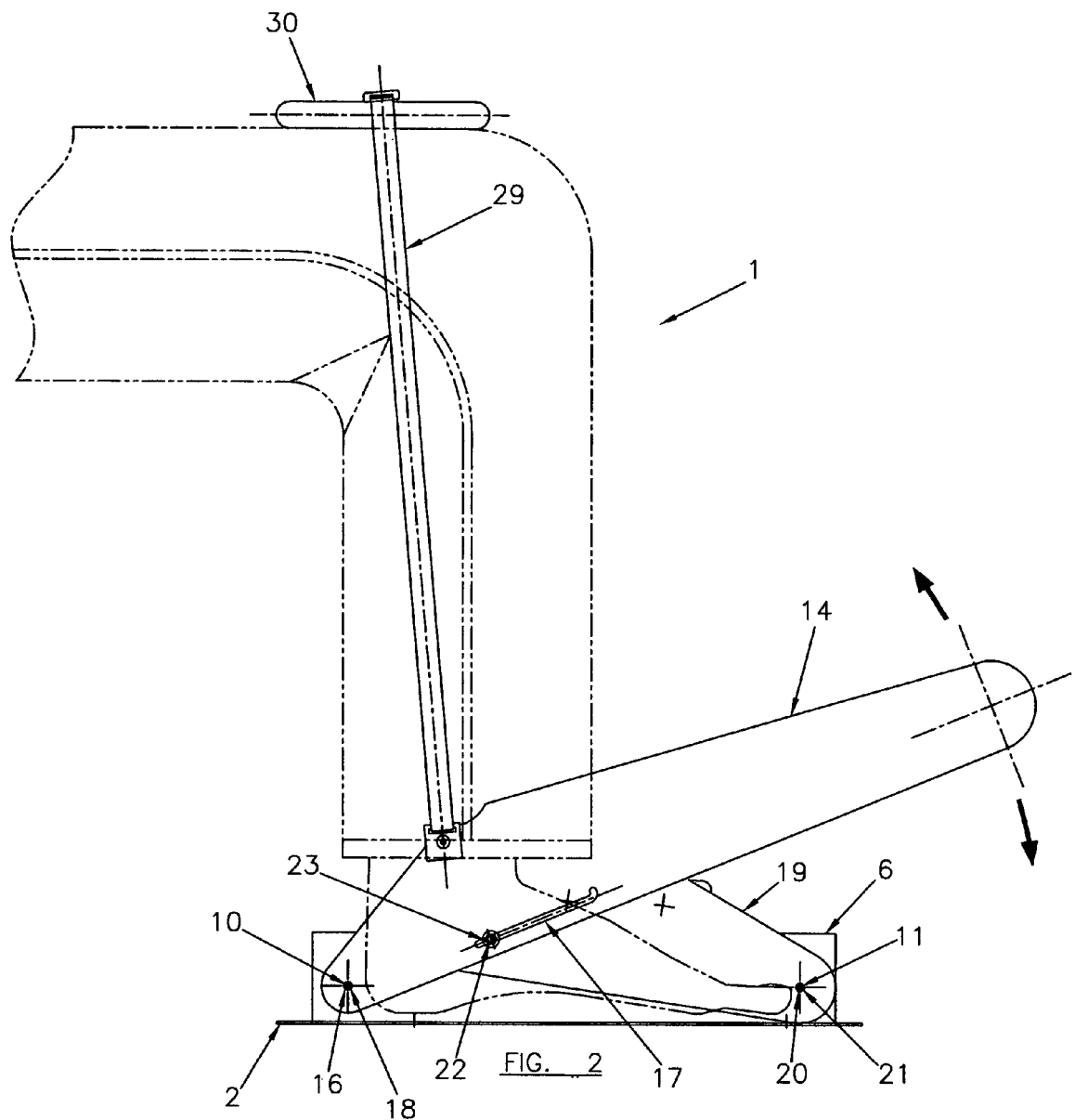

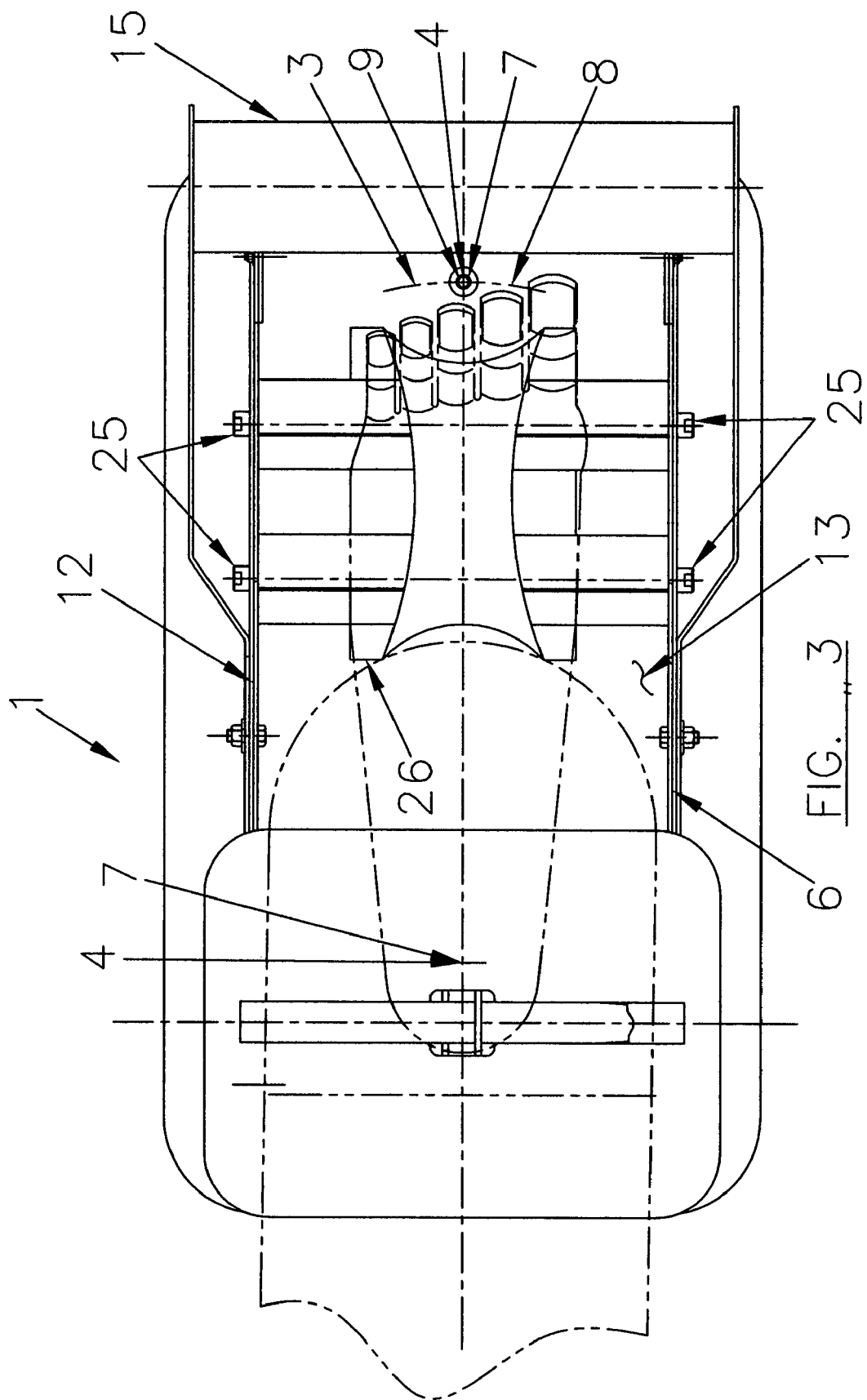

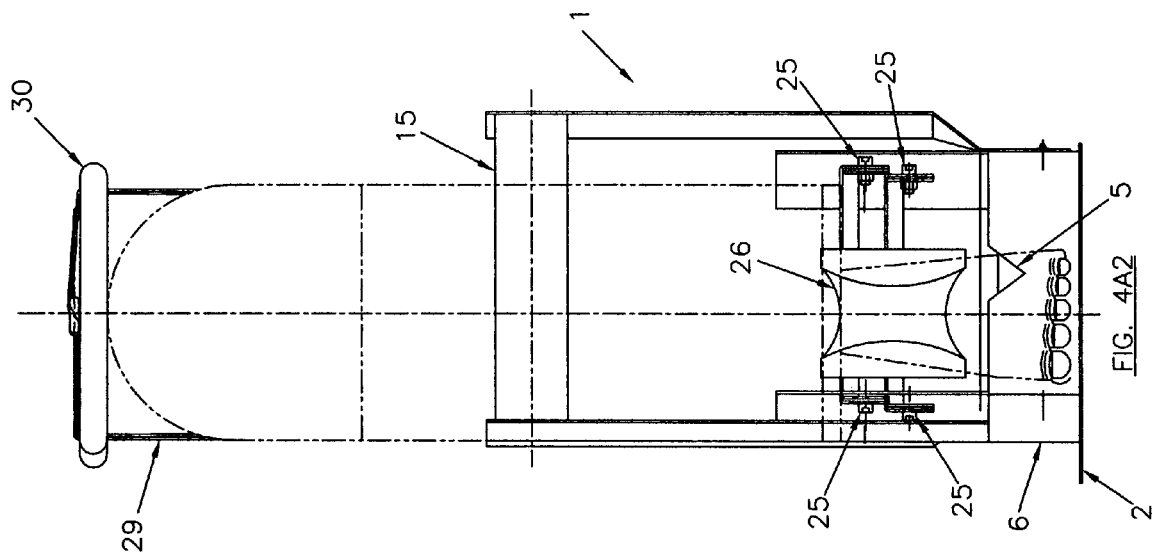
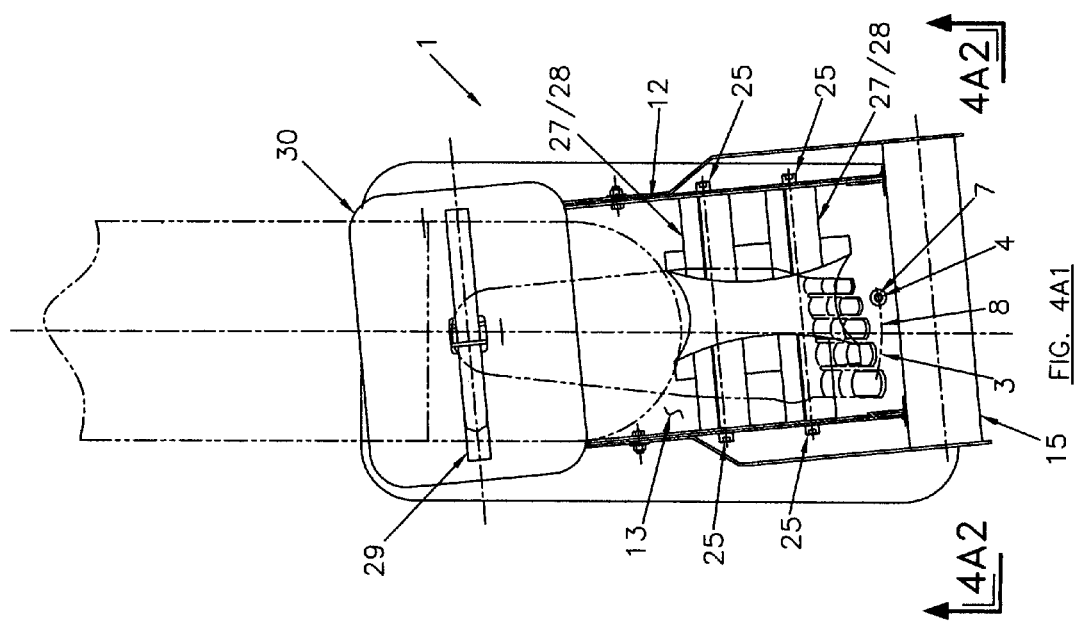

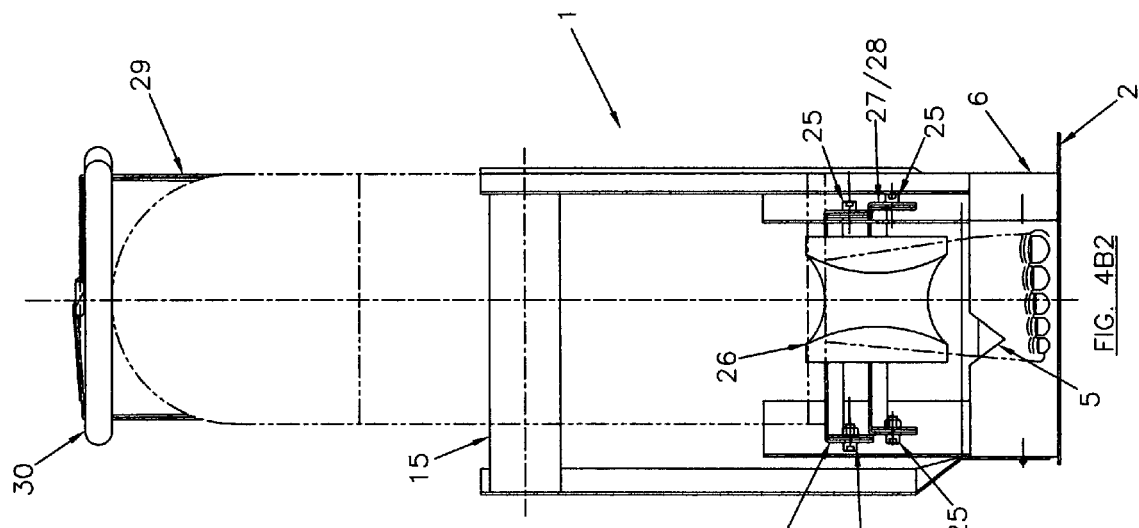
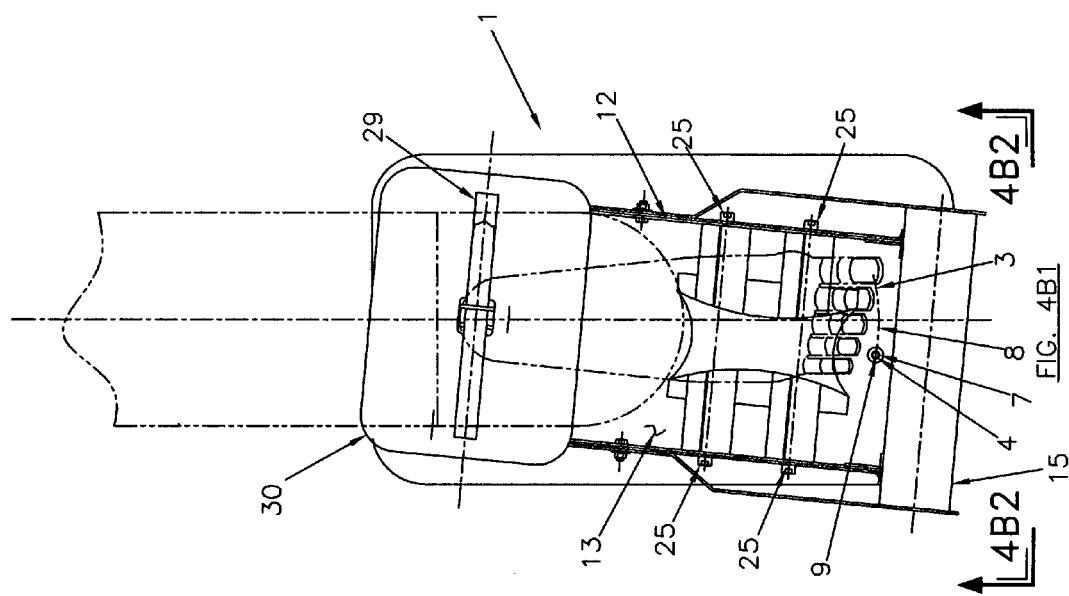

METHOD AND APPARATUS FOR MAKING FOOT IMPRESSIONS

BACKGROUND OF THE INVENTION AND SUMMARY OF THE INVENTION

The present invention relates generally to a method and device which facilitates the taking of an impression of a person's foot. That impression can then be used in the manufacture of custom full contact orthotics. The method and apparatus include a generally rectangular box of foam, that will be deformed by the person's foot during the casting process, and the box is placed in a receptacle. The receptacle is supported on a generally planer base and can swivel or rotate so that the person's knee will be put into a neutral position. The amount of swiveling movement of the mold-receiving receptacle can be calibrated and set. In use, the person is placed in a seated position, and a box of foam is placed in the receptacle. A strap assembly is used to exert a downward force on the person's lower leg. The strap is secured to a lever arm of the apparatus. A lever mechanism is useable to exert a downward pressure on a arch-engaging block which is situated above the box of foam. The block pushes the foot down into the foam. The block is slideable transversely to the box of foam thus insuring that the block exerts its downward pressure directly on the arch of the foot. The lever mechanism is a two-armed assembly with a lever arm pivotedly secured to one end of the foam box receptacle and a block arm pivotedly secured to the opposite end of the foam box receptacle and securing the block above the foam box receptacle and adapted so that the operator in use pushes the lever arm downward causing the block to correspondingly push the person's foot down into the foam thus making an impression of the person's foot in the foam. The block arm of the assembly pivots on the lever arm and slides along a channel within the lever arm allowing the block to push downward on the person's foot when the lever arm is pushed downward by the operator. The ankle and forefoot are set at the same time making full contact of the foot in the foam with the foot in neutral position.

The method and apparatus provide exceptional advantages when employed in the orthotic field. The present method and apparatus are simple and inexpensive in construction and allows for positioning a person's leg, ankle and foot in a 90 degree neutral position in making the impression of the person's foot, thus insuring a correct fit for the orthotics ultimately manufactured from the foot impression. In addition, a strap assembly of the apparatus is adjustable and secures the person's leg, ankle and knee in a neutral position during the making of the impression of the person's foot.

A further advantage of the present method and apparatus is the adjustable block which can be slideably moved transversely to the foam box to be in direct alignment with the arch of person's foot during the foot impression process, thus allowing even pressure to be placed on the person's foot and insuring consistent foot impressions.

Heretofore, the prior art has disclosed patents for a lever arm with a pressed block that is sized to be received in a mold; an arch support forming device with pads that engage the foot, an apparatus for the production of an orthopedic foot rest or support engaged by a block, an apparatus for use in making insoles with receiving boxes that pivot on a support plate provided with markings; and an apparatus for molding shoe inserts with straps for use in positioning the person's foot. Some of the patents of the prior art are listed as follows:

| | | |
|---|---|---|
| U.S. Pat. No. 584,693 | Marshall | Jun. 15, 1897 |
| U.S. Pat. No. 1,638,696 | Lewis | Aug. 9, 1927 |
| U.S. Pat. No. 2,487,965 | Dresser | Nov. 15, 1949 |
| U.S. Pat. No. 3,458,898 | Casparis | Aug. 5, 1969 |
| U.S. Pat. No. 4,747,989 | Peterson | May 31, 1988 |
| U.S. Pat. No. 5,928,673 | Ryan | Jul. 27, 1999 |
| U.S. Pat. No. 1,044,171 | Guilford | Nov. 12, 1912 |
| U.S. Pat. No. 2,177,304 | Murray | Oct. 24, 1939 |
| U.S. Pat. No. 2,613,398 | Crowell | Oct. 14, 1952 |
| U.S. Pat. No. 4,139,337 | David, et al. | Feb. 13, 1979 |
| U.S. Pat. No. 5,593,699 | Grassi | Jan. 14, 1997 |

The prior art as set forth above discloses some individual features of the present method and apparatus but does not disclose the specific structure of the present method and apparatus and the novelty of the present method and apparatus.

U.S. Pat. No. 584,693 issued to Marshall on Jun. 15, 1897, pertains to a butter-mold and discloses a lever arm with a press block that is sized to be received in a mold but does not provide for an adjustable receptacle on a base plate with calibrations, a slideably adjustable block, or an adjustable strap to make consistent foot impressions as does the present method and apparatus.

U.S. Pat. No. 1,044,171 issued to Guilford on Nov. 12, 1912, pertains to a method of forming arch supports and teaches of pads that engage the foot but does not provide for an adjustable receptacle on a base plate with calibrations, a slideably adjustable block, or an adjustable strap to make consistent foot impressions as does the present method and apparatus.

U.S. Pat. No. 3,458,898 issued to Casparis on Aug. 5, 1969, teaches of an apparatus for the production of an orthopedic foot rest or support wherein a block engages the foot but does not provide for an adjustable receptacle on a base plate with calibrations, a slideably adjustable block, or an adjustable strap to make consistent foot impressions as does the present method and apparatus.

U.S. Pat. No. 5,593,699 issued to Grassi on Jan. 14, 1997, pertains to an apparatus for manufacturing form-fitting insoles wherein the apparatus provides for two-foot receiving boxes which pivot on a support plate and a spongy material placed in a box in each mold but does not provide for an adjustable receptacle on a base plate with calibrations, slideably adjustable block, or an adjustable strap to make consistent foot impressions as does the present method and apparatus.

U.S. Pat. No. 5,928,673 issued to Ryan on Jul. 27, 1999, pertains to an apparatus for molding shoe inserts wherein the apparatus depicts straps for use in positioning a person's foot but does not provide for an adjustable receptacle on a base plate with calibrations, slideably adjustable block, or an adjustable strap to make consistent foot impressions as does the present method and apparatus.

BRIEF DESCRIPTION OF THE DRAWINGS

FIG. 1 is a side view of the entire invention in open position.

FIG. 1A is an end view of the entire invention in open position.

FIG. 2 is a side view of the entire invention in engaged position.

FIG. 3 is a plan view of the entire invention in neutral position.

FIG. 4A1 is a plan view of the entire invention in adjusted position.

FIG. 4A2 is an end view of the entire invention in adjusted position.

FIG. 4B1 is a plan view of the entire invention in adjusted position.

FIG. 4B2 is an end view of the entire invention in adjusted position.

ABSTRACT OF THE DISCLOSURE

1. Entire invention
2. Base
3. Base adjustment channel
4. Base pivot hole
5. Base calibration
6. Foam Box receptacle
7. Foam box pivot hole
8. Foam box adjustment channel
9. Base fastening means
10. Lever arm pivot pin
11. Block arm pivot pin
12. Foam box
13. Foam
14. Lever Arm
15. Lever Handle
16. Lever arm pivot hole
17. Lever arm slide channel
18. Lever arm fastening means
19. Block arm
20. Block arm pivot hole
21. Block arm fastening means
22. Block arm slide pin
23. Block arm slide pin fastening means
24. Block slide adjuster hole
25. Block slide adjuster fastening means
26. Block
27. Block slide adjuster channel
28. Block side adjuster
29. Adjustable strap
30. Adjustable strap pad

DETAILED DESCRIPTION OF THE DRAWINGS

Reference is now made to the drawings wherein the present invention is illustrated in detail and wherein similar components bear the same reference numeral throughout the several views. FIG. 1 illustrates a side view of the preferred embodiment of the invention, the entire invention generally referred to as numeral 1 as illustrated with base 2, lever arm pivot pin 10, block arm pivot pin 11, lever arm 14, lever arm pivot hole 16, lever arm slide channel 17, lever arm fastening means 18, block arm 19, block arm pivot hole 20, block arm fastening means 21, block arm slide pin 22, block arm slide pin fastening means 23, block slide adjuster hole 24, block slide adjuster fastening means 25, adjustable strap 29, and adjustable strap pad 30.

FIG. 1A illustrates an end view of the preferred embodiment of the invention in open position, the entire invention generally referred to by numeral 1 is illustrated with base 2, base calibration 5, lever handle 15, block slide adjuster fastening means 25, block 26, block slide adjuster channel 27, block slide adjuster 28, adjustable strap 29, and adjustable strap pad 30.

FIG. 2 illustrates a side view of the preferred embodiment of the entire invention in engaged position, the entire invention generally referred to as numeral 1 is illustrated with base 2, foam box receptacle 6, lever arm pivot pin 10, block arm pivot pin 11, lever arm 14, lever arm pivot hole 16, lever arm slide channel 17, lever arm fastening means 18, block arm 19, block arm pivot hole 20, block arm fastening means 21, block arm slide pin 22, block arm slide pin fastening means 23, block arm slide pin fastening means 23, adjustable strap 29, and adjustable strap pad 30.

FIG. 3 illustrates a plan view of the preferred embodiment of the entire invention in neutral position, the entire invention generally referred to as numeral 1 is illustrated with base adjustment channel 3, base pivot hole 4, foam box receptacle 6, foam box pivot hole 7, foam box adjustment channel 8, base fastening means 9, foam box 12, foam 13, lever handle 15, block slide adjuster fastening means 25, and block 26.

FIG. 4A1 illustrates a plan view of the preferred embodiment of the entire invention in adjusted position, the entire invention generally referred to as numeral 1 is illustrated with base adjustment channel 3, base pivot hole 4, foam box adjustment channel 8, foam box 12, foam 13, lever handle 15, block slide adjuster fastening means 25, block slide adjuster channel 27, block slide adjuster 28, adjustable strap 29, and adjustable strap pad 30.

FIG. 4A2 illustrates an end view of the preferred embodiment of the entire invention in adjusted position, the entire invention generally referred to as numeral 1 is illustrated with base 2, base calibration 5, foam box receptacle 6, lever handle 15, block slide adjuster fastening means 25, block 26, adjustable strap 29, and adjustable strap pad 30.

FIG. 4B1 illustrates a plan view of the preferred embodiment of the entire invention in adjusted position, the entire invention generally referred to as numeral 1 is illustrated with base adjustment channel 3, base pivot hole 4, foam box pivot hole 7, foam box adjustment channel 8, base fastening means 9, foam box 12, foam 13, lever handle 15, block slide adjuster fastening means 25, adjustable strap 29, and adjustable strap pad 30.

FIG. 4B2 illustrates an end view of the preferred embodiment of the entire invention in adjusted position, the entire invention generally referred to as numeral 1 is illustrated with base 2, base calibration 5, foam box receptacle 6, lever handle 15, block slide adjuster fastening means 25, block 26, block slide adjuster channel 27, block slide adjuster 28, adjustable strap 29, and adjustable strap pad 30.

DESCRIPTION OF THE PREFERRED EMBODIMENT

Referring to FIGS. 1 through 4B2 the preferred embodiment of the present invention is a method and apparatus for taking an impression of a person's foot which impression can then be used in the manufacture of orthotics. The apparatus comprises a rectangular box filled with foam which will be deformed by the person's foot during the impression process which box is placed in a rectangular foam box receptacle that is secured to a planer generally rectangular base and adapted to swivel or rotate on said base with said foam box receptacle adapted with a channel on the bottom at one end and a pivot hole on the bottom of the opposite end to swivel or rotate on the base and adapted to be adjusted at markings on the base to insure the neutral position of the person's leg, foot and ankle in the making of the foot impression. The foam box receptacle is adapted with pins at one end of the box to receive a lever arm which pivotely moves up and away and/or down and towards the foam box receptacle and the foam box receptacle is adapted at the opposite end with pins to receive a block arm to pivotedly move up and away and down toward the foam box receptacle, said lever arm and block arm adapted to pivotedly move with one another to move the block arm up and away from or down and towards the foam box receptacle as the lever arm is raised or lowered respectively. A lever arm is provided which is generally u-shaped with a handle formed at the u end and the legs of the u adopted to pivotedly secure to pins at one end of the foam box receptacle and providing a channel in each leg of the u to except and allow a block arm to slide within. A block arm of generally h-shape and at one end of the h adapted to pivotedly engage with pins at the opposite end of the foam receptacle box and at the other h end adapted to slide within the channels of the lever arm to move the block arm up and away from the foam receptacle box or down and toward the foam receptacle box upon corresponding movement of the lever arm. The h portion of the block arm is comprised of two members engaged and adapted to accept a block to slide between the legs of the block arm transversely to the box of foam and adapted to be centered on the arch of person's foot in the making of the foot impression. A block of general rectangular shape is further provided to adjustably slide along the members of the block arm and transversely to the box of foam to align with the arch of person's foot in the making of the foot impression. Further an adjustable strap is secured at the ends of the legs of the lever arm and is provided with a pad to adjust to and engage the person's knee and to insure uniform pressure on the person's leg, ankle and foot in the making of the foot impression.

Although the invention has been described in preferred form with a certain degree of particularity, it is understood that the present disclosure of the preferred form has been made only by way of example and numerous changes in the details of construction and the combination arrangement of parts may be resorted to without departing from the spirit and scope of the invention as herein after claimed.

What is claimed is:

1. A device for taking an impression of a person's foot which impression can then be used in the manufacture of orthotics comprising a box filled with foam that will be deformed by the person's foot during the impression process, which foam box is placed in a foam box receptacle, the foam box receptacle being adapted to swivel or rotate on a base and which swiveling or rotating movement can be calibrated and adjusted to insure the neutral position of the person's leg, foot, knee and ankle in the making of the foot impression, a lever mechanism useable to exert a downward pressure on an arch-engaging block situated above the box of foam, the block slideable transversely to the box of foam to insure that the block exerts an even downward pressure directly on the arch of the foot, the lever apparatus comprising a two-arm assembly with an over-center component of movement and a strap assembly used to exert a downward force on the person's lower leg, with the strap secured to the lever assembly of the device.

2. The foot impression device of claim 1 wherein the foam box receptacle is rectangular is provided with a pivot hole on the bottom of one end and a channel on the bottom of the opposite end and adapted to be secured with pins to the base to provide for adjustable rotating or swiveling movement of the foam box receptacle on the base and wherein the base is calibrated at the channel end of the box and a means is provided to set the foam receptacle box in a selected position to insure the neutral position of the person's leg, foot, and ankle in the making of the foot impression.

3. The foot impression device of claim 1 wherein the lever mechanism is a lever arm which pivotedly moves up and away and/or down and towards the foam box receptacle and is pivotedly secured by means at one end of the foam box receptacle and is adapted to engage with a block arm which block arm is adapted to pivotedly move up and away and/or down and toward the foam box receptacle correspondingly with the upward or downward movement of the lever arm with the block arm pivotedly secured to the opposite end of the foam box receptacle.

4. The foot impression device of claim 3 wherein the lever arm is generally u-shaped with a handle formed at the u end and the legs of the u are pivotedly secured to pins on the foam box receptacle and a channel is formed in each leg of the u to accept and allow the block arm to slide within and the block arm is generally h-shaped and at one end of the h pivotedly secured by means to the opposite end of the foam box receptacle and at the opposite h end adapted with pins to slide within the channels of the lever arm and with the h portion of the block arm comprising two members adapted to allow the block to slide back and forth between the legs of the block arm and wherein the block is provided with channels through the block to allow the block to slide on the members secured to the legs of the block arm.

5. The foot impression device of claim 1 wherein the adjustable strap is secured by means to the lever arm of the lever assembly and moves upward or downward toward the box of foam with the corresponding upward or downward movement of the lever arm and wherein the adjustable strap is provided with a pad to adjust to and engage the person's knee and to insure uniform pressure on the person's leg, ankle and foot in the making of the foot impression.

6. A method for taking an impression of a person's foot which impression can then be used in the manufacture of orthotics, said method comprising the steps of:

The person is placed in a seated position,

A box of foam that will be deformed by the person's foot during the impression process is placed in a foam box receptacle, Said foam box receptacle is secured to the base of a foot impression device and adapted to swivel or rotate on said base so that the person's leg, foot, knee, and ankle will be put into a neutral position wherein the rotating or swiveling movement can be calibrated and set, A strap assembly of said device secured to a lever mechanism of said device is adjusted and secured to the person's knee and is used to exert a down-ward force on the person's knee, Said lever mechanism of said device is useable to exert a downward pressure on an arch engaging block which is situated above the box of foamy, Said block pushes the foot of the person down into the foam making a full contact foot impression, Said block is slideable transversely to the box of foam which insures that said block exerts its downward pressure directly on the arch of the foot of the person insuring an even downward pressure directly on the arch of the foot.

7. The method of claim No. 6 wherein the foam box receptacle is rectangular is provided with a pivot hole on the bottom of one end and a channel on the bottom of the opposite end and adapted to be secured with pins to the base to provide for adjustable rotating or swiveling movement of the foam box receptacle on the base and wherein the base is calibrated at the channel end of the fox and a means is provided to set the foam receptacle box in a selected position to insure the neutral position of the person's leg, foot, and ankle in the making of the foot impression.

8. The method of claim No. 6 wherein the lever mechanism is a lever arm which pivotedly moves up and away and/or down and towards the foam box receptacle and is pivotedly secured by means at one end of the foam box receptacle and is adapted to engage with a block arm which block arm is adapted to pivotedly move up and away and/or down and toward the foam box receptacle correspondingly with the upward or downward movement of the lever arm with the block arm pivotedly secured to the opposite end of the foam box receptacle.

9. The method of claim No. 6 wherein the lever arm is generally u-shaped with a handle formed at the u end and the legs of the u are pivotedly secured to pins on the foam box receptacle and a channel is formed in each leg of the u to accept and allow the block arm to slide within and the block arm is generally h-shaped and at one end of the h pivotedly secured by means to the opposite end of the foam box receptacle and at the opposite h end adapted with pins to slide within the channels of the lever arm and with the h portion of the block arm comprising two members adapted to allow the block to slide back and forth between the legs of the block arm and wherein the block is provided with channels through the block to allow the block to slide on the members secured to the legs of the block arm.

10. The method of claim No. 6 wherein the adjustable strap is secured by means to the lever arm of the lever assembly and moves upward or downward toward the box of foam with the corresponding upward or downward movement of the lever arm and wherein the adjustable strap is provided with a pad to adjust to and engage the person's knee and to insure uniform pressure on the person's leg, ankle and foot in the making of the foot impression.

\* \* \* \* \*